（12）United States Patent
Pittman et al.

(10) Patent No.: US 11,612,720 B2
(45) Date of Patent: Mar. 28, 2023

(54) EXIT PATH CONNECTOR FOR CATHETER ASSEMBLY

(71) Applicant: Creganna Unlimited Company, Galway (IE)

(72) Inventors: Brandon Pittman, Albertville, MN (US); Jason Bromen, Nowthen, MN (US)

(73) Assignee: CREGANNA UNLIMITED COMPANY, Galway (IE)

( * ) Notice: Subject to any disclaimer, the term of this patent is extended or adjusted under 35 U.S.C. 154(b) by 105 days.

(21) Appl. No.: 17/008,849

(22) Filed: Sep. 1, 2020

(65) Prior Publication Data
US 2021/0077780 A1    Mar. 18, 2021

Related U.S. Application Data

(60) Provisional application No. 62/905,860, filed on Sep. 25, 2019, provisional application No. 62/900,208, filed on Sep. 13, 2019.

(51) Int. Cl.
*A61M 25/01*    (2006.01)
*A61M 25/00*    (2006.01)
*A61M 39/10*    (2006.01)

(52) U.S. Cl.
CPC .... *A61M 25/0147* (2013.01); *A61M 25/0052* (2013.01); *A61M 25/0097* (2013.01);
(Continued)

(58) Field of Classification Search
CPC .......... A61M 2039/1077; A61M 39/10; A61M 39/105; A61M 25/052; A61M 25/0147;
(Continued)

(56) References Cited

U.S. PATENT DOCUMENTS 5,352,215 A * 10/1994 Thome .................. A61M 39/10
  604/533
5,374,245 A * 12/1994 Mahurkar ........... A61M 25/005
  604/43
(Continued)

FOREIGN PATENT DOCUMENTS

DE    102018209087 A1 * 12/2019
EP       1518582 A1 *  3/2005  ........ A61M 25/0029
(Continued)

OTHER PUBLICATIONS

European Search Report for European Application No. 20195729.7, dated Feb. 24, 2021.

*Primary Examiner* — Katherine H Schwiker
*Assistant Examiner* — Adam J. Cermak

(57) ABSTRACT

A catheter assembly includes an outer shaft having an outer shaft body forming an outer shaft bore that receives an inner shaft. The outer shaft has a wire transition section. The catheter assembly includes an exit path connector coupled to the outer shaft body at the wire transition section. The exit path connector has a rigid body section separate and discrete from the outer shaft body and coupled to the outer shaft body. The body section defines an exit path connector bore that receives the inner shaft. The body section has a side exit port at a side of the body section being open to the exit path connector bore. The catheter assembly includes a catheter wire passing through the side exit port from an interior to an exterior of the cable exit port.

24 Claims, 10 Drawing Sheets

(52) U.S. Cl.
CPC ..... *A61M 25/0136* (2013.01); *A61M 25/0045* (2013.01); *A61M 39/10* (2013.01); *A61M 2025/0004* (2013.01); *A61M 2025/015* (2013.01)

(58) Field of Classification Search
CPC .......... A61M 25/0133; A61M 25/0136; A61M 25/0097; A61M 2025/0183; A61M 2025/015; A61M 2025/0161
See application file for complete search history.

(56) References Cited

U.S. PATENT DOCUMENTS

| | | | | |
|---|---|---|---|---|
| 5,951,495 | A * | 9/1999 | Berg | A61M 25/005 600/585 |
| 7,402,151 | B2 * | 7/2008 | Rosenman | A61M 25/0147 604/528 |
| 8,556,850 | B2 * | 10/2013 | Tegg | A61M 25/0136 604/95.04 |
| 10,076,638 | B2 * | 9/2018 | Tran | A61F 2/2436 |
| 10,595,820 | B2 * | 3/2020 | Stigall | A61B 8/12 |
| 10,603,197 | B2 * | 3/2020 | Marmur | A61F 2/07 |
| 2002/0026129 | A1 * | 2/2002 | White | A61M 25/00 600/585 |
| 2005/0049574 | A1 * | 3/2005 | Petrick | A61M 25/0068 604/525 |
| 2005/0267442 | A1 * | 12/2005 | Von Oepen | A61M 25/0043 604/509 |
| 2006/0079787 | A1 * | 4/2006 | Whiting | A61M 25/0041 600/466 |
| 2006/0100687 | A1 | 5/2006 | Fahey et al. | |
| 2006/0142703 | A1 * | 6/2006 | Carter | A61M 25/0015 264/138 |
| 2006/0241564 | A1 | 10/2006 | Corcoran et al. | |
| 2007/0282358 | A1 * | 12/2007 | Remiszewski | A61B 1/0057 606/159 |
| 2009/0182200 | A1 * | 7/2009 | Golden | A61M 25/09 600/153 |
| 2010/0160858 | A1 * | 6/2010 | Fischer | A61M 25/0136 604/95.04 |
| 2012/0136340 | A1 * | 5/2012 | Tanioka | A61M 25/0169 604/526 |
| 2014/0135686 | A1 * | 5/2014 | Jimenez | A61M 25/0147 604/95.04 |
| 2014/0188054 | A1 * | 7/2014 | Iijima | A61M 25/0052 604/523 |
| 2015/0032086 | A1 * | 1/2015 | Hopkinson | A61M 25/0032 604/509 |
| 2016/0058975 | A1 * | 3/2016 | Kimmel | A61M 25/0147 600/411 |
| 2016/0158497 | A1 * | 6/2016 | Tran | A61M 25/0071 604/95.04 |
| 2018/0021546 | A1 | 1/2018 | McDermott et al. | |
| 2018/0229009 | A1 * | 8/2018 | Campbell | A61M 25/0029 |
| 2019/0351179 | A1 * | 11/2019 | Ishida | A61M 25/0029 |
| 2019/0357893 | A1 * | 11/2019 | Weber | A61B 17/00234 |
| 2020/0016370 | A1 * | 1/2020 | Sasaki | A61M 25/005 |
| 2020/0038628 | A1 * | 2/2020 | Chou | A61M 25/0052 |
| 2020/0121361 | A1 * | 4/2020 | Hashi | A61B 90/50 |
| 2020/0179661 | A1 * | 6/2020 | Fischell | A61M 25/0053 |
| 2020/0222667 | A1 * | 7/2020 | Tang | A61M 25/0147 |
| 2020/0230371 | A1 * | 7/2020 | Klausen | A61M 25/0108 |
| 2020/0246591 | A1 * | 8/2020 | Bogusky | A61M 25/0012 |
| 2021/0001107 | A1 * | 1/2021 | Beach | A61M 39/1011 |
| 2021/0016063 | A1 * | 1/2021 | Drake | A61M 25/0136 |
| 2021/0338983 | A1 * | 11/2021 | Zhang | A61M 39/1011 |
| 2022/0079666 | A1 * | 3/2022 | Ku | A61M 25/0138 |

FOREIGN PATENT DOCUMENTS

| | | | | |
|---|---|---|---|---|
| EP | 2495006 | A1 * | 9/2012 | ........ A61M 25/0102 |
| EP | 2979721 | B1 * | 12/2016 | .......... A61M 25/005 |
| EP | 3669746 | A1 * | 6/2020 | |
| FR | 2462912 | A1 * | 2/1981 | ........ A61M 25/0102 |
| JP | 2002355313 | A | 12/2002 | |
| JP | 2008522734 | A * | 7/2008 | .............. A61F 2/88 |
| WO | WO-9414495 | A1 * | 7/1994 | .............. A61F 2/88 |
| WO | WO-9728839 | A1 * | 8/1997 | ......... A61B 1/00105 |
| WO | WO-9944667 | A1 * | 9/1999 | ........ A61M 25/0054 |
| WO | WO-03/037418 | A2 | 5/2003 | |
| WO | WO-03037418 | A2 * | 5/2003 | ........ A61M 25/0052 |
| WO | WO-2006127929 | A2 * | 11/2006 | ........ A61M 25/0032 |
| WO | WO-2014/156600 | A1 | 10/2014 | |
| WO | WO-2014156600 | A1 * | 10/2014 | ........ A61M 25/0045 |
| WO | WO-2015013622 | A1 * | 1/2015 | ........ A61M 25/0032 |
| WO | WO-2018067824 | A1 * | 4/2018 | ........ A61M 25/0021 |
| WO | WO-2020106705 | A1 * | 5/2020 | ........... A61F 2/2427 |
| WO | WO-2020135456 | A1 * | 7/2020 | .............. A61F 2/962 |

* cited by examiner

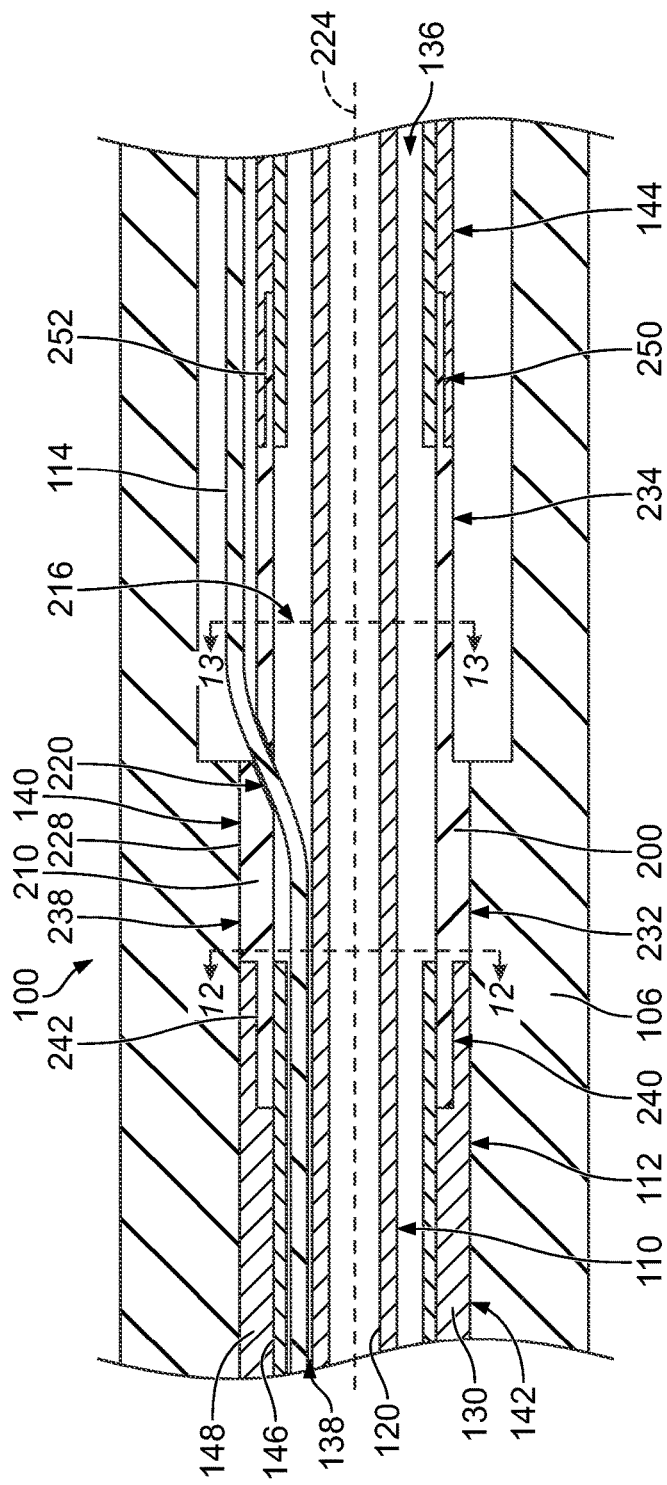
FIG. 11
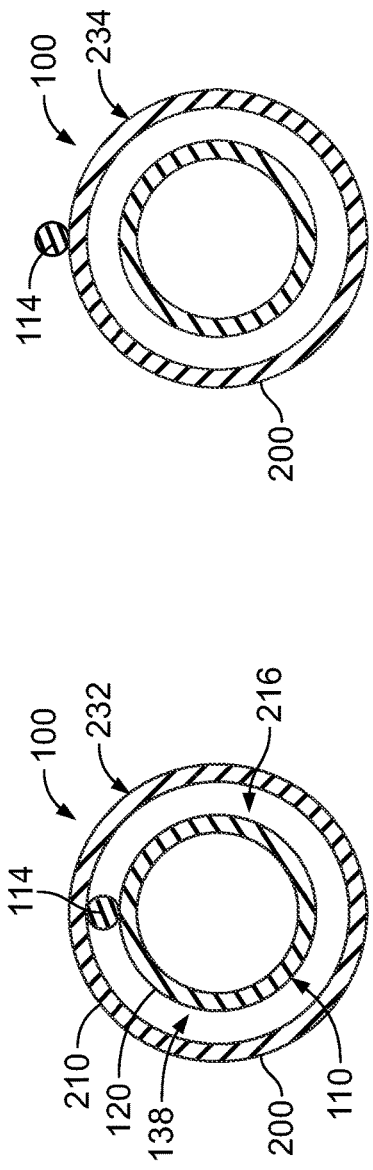
FIG. 12
FIG. 13

EXIT PATH CONNECTOR FOR CATHETER ASSEMBLY

CROSS-REFERENCE TO RELATED APPLICATIONS

This application claims priority to U.S. Provisional Application No. 62/900,208, filed 13 Sep. 2019, titled "EXIT PATH CONNECTOR FOR CATHETER ASSEMBLY," and U.S. Provisional Application No. 62/905,860, filed 25 Sep. 2019, titled "EXIT PATH CONNECTOR FOR CATHETER ASSEMBLY," both of which are incorporated by reference herein in their entirety.

BACKGROUND OF THE INVENTION

The subject matter herein relates generally to catheter assemblies.

Catheter assemblies are used during medical procedures for monitoring a patient or for performing a medical procedure on a patient. Some known catheter assemblies include wires extending the length of the catheter, such as for monitoring the patient at the distal end of the catheter or for actuating the distal end of the catheter for steering the catheter into position. The catheter wires are typically routed through the interior of the catheter assembly. However, the catheter wires exit through the side of the catheter body to connect to an actuator or monitoring device. The wire exits are typically formed by cutting or slicing the outer shaft of the catheter to form wire exit openings. Such wire exit openings can create an area of weakness or potential failure. Additionally, the wire exit openings are typically formed in multiple processing steps. Forming the proper wire exit angle and wire exit position may be difficult to control due to the flow of material during the forming process. The wire exit forming process is typically performed manually leading to inconsistent forming.

A need remains for a reliable and cost effective catheter assembly having wire exit openings for routing wires within the catheter assembly.

BRIEF DESCRIPTION OF THE INVENTION

In one embodiment, a catheter assembly is provided including an inner shaft extending between a proximal end and a distal end and an outer shaft extending between a proximal end and a distal end. The outer shaft includes an outer shaft body forming an outer shaft bore that receives the inner shaft. The outer shaft has a wire transition section proximate to the proximal end. The catheter assembly includes an exit path connector coupled to the outer shaft body at the wire transition section. The exit path connector has a rigid body section separate and discrete from the outer shaft body and coupled to the outer shaft body. The body section defines an exit path connector bore that receives the inner shaft. The body section has a side exit port at a side of the body section being open to the exit path connector bore. The catheter assembly includes a catheter wire extending between the distal end and the proximal end of the outer shaft. The catheter wire passes through the side exit port from an interior of the cable exit connector to an exterior of the cable exit port. The catheter wire extends within the outer shaft bore from the exit path connector to the distal end of the outer shaft.

Optionally, the body section of the exit path connector may be manufactured from a different material as a material of the outer shaft body. The outer shaft may be discontinuous at the wire transition section including a forward section and a rearward section with the exit path connector being positioned between and connecting the forward section and the rearward section.

Optionally, the outer shaft may include an inner layer defining the outer shaft bore. The exit path connector may be coupled to the inner layer at a seam. The outer shaft may include an outer layer formed in situ around the inner layer and the exit path connector at the seam.

Optionally, the exit path connector may include a front joining section extending forward of the body section. The front joining section may be coupled to the outer shaft body. The front joining section may include lap joints coupled to the outer shaft. The outer shaft may include an inner layer defining the outer shaft bore and an outer layer surrounding an exterior of the inner layer. The front joining section may be coupled to the inner layer at a seam. The outer layer may be seamlessly coupled to the inner layer and the joining section at the seam. The exit path connector may include a rear joining section extending rearward of the body section. The rear joining section may be coupled to the outer shaft body.

Optionally, the body section may include an inner surface and an outer surface. The inner surface may define the exit path connector bore. The side exit port may extend between the inner surface and the outer surface at an angle transverse to a bore axis of the exit path connector bore.

Optionally, the catheter assembly may include a handle coupled to the outer shaft at the proximal end. The handle may have a handle bore that receives the proximal end of the outer shaft and the exit path connector. The catheter wire may exit the side exit port into the handle bore. The exit path connector may include a handle mount coupled to the handle.

Optionally, the body section of the exit path connector may be stainless steel. The body section of the exit path connector may be a 3D printed body section.

Optionally, the cable exit connector may extend between a front and a rear. The side exit port may be positioned a predetermined distance from the front. The side exit port may extend at a predetermined angle relative to a bore axis of the exit path connector bore.

Optionally, the body section of the cable exit connector may include a front hub and a rear hub. The front hub may have a larger diameter than the rear hub. A shoulder may be formed between the front hub and the rear hub. The side exit port may pass through the shoulder. The front hub may be thicker than the rear hub.

Optionally, the exit path connector may include a second side exit port receiving a second catheter wire. The catheter wire may be a pull wire used to actuate at least one of the distal end of the inner shaft or the distal end of the outer shaft. The catheter assembly may include a wire lumen receiving the catheter wire. The wire lumen may pass through the side exit port.

In an embodiment, a catheter assembly is provided including an inner shaft extending between a proximal end and a distal end and an outer shaft extending between a proximal end and a distal end. The outer shaft includes an outer shaft body forming an outer shaft bore that receives the inner shaft. The outer shaft has a wire transition section proximate to the proximal end. The catheter assembly includes an exit path connector coupled to the outer shaft body at the wire transition section. The exit path connector has a front joining section, a rear joining section, and a body section between the front joining section and the rear joining section. The exit path connector is separate and discrete from the outer shaft body. The front joining section is coupled to the outer shaft body and the rear joining section is coupled to the outer shaft body. The body section has an inner surface and an outer surface. The inner surface defines an exit path connector bore extending along a bore axis. The exit path connector bore receives the inner shaft. The body section has a side exit port at a side of the body section. The side exit port extends between the inner surface and the outer surface at an angle transverse to the bore axis. The catheter assembly includes a catheter wire extending between the distal end and the proximal end of the outer shaft. The catheter wire passes through the side exit port. The catheter wire passes along the inner surface of the body section forward of the side exit port. The catheter wire passes along the outer surface of the body section rearward of the side exit port. The catheter wire extends within the outer shaft bore from the exit path connector to the distal end of the outer shaft.

In another embodiment, an exit path connector is provided for a catheter assembly including an inner shaft, an outer shaft, and a catheter wire extending between a distal end and a proximal end of the catheter assembly. The exit path connector includes a front joining section having front joining features and front openings between the front joining features. The front joining features are configured to engage an inner layer of the outer shaft and the front openings are configured to receive polymer material of an outer layer surrounding the inner layer and the front joining features. The exit path connector includes a rear joining section having rear joining features and rear openings between the rear joining features. The rear joining features are configured to engage the inner layer of the outer shaft and the rear openings are configured to receive polymer material of the outer layer surrounding the inner layer and the rear joining features. The exit path connector includes a body section between the front joining section and the rear joining section. The body section has an inner surface and an outer surface. The inner surface defines an exit path connector bore configured to receive the inner shaft. The exit path connector bore extends along a bore axis. The body section has a side exit port at a side of the body section configured to receive the catheter wire. The side exit port extends between the inner surface and the outer surface at an angle transverse to the bore axis.

BRIEF DESCRIPTION OF THE DRAWINGS

FIG. 11 is a cross-sectional view of a portion of the catheter assembly in accordance with an exemplary embodiment.

FIG. 12 is a cross-sectional view of a portion of the catheter assembly in accordance with an exemplary embodiment.

FIG. 13 is a cross-sectional view of a portion of the catheter assembly in accordance with an exemplary embodiment

DETAILED DESCRIPTION OF THE INVENTION

Figure 1:
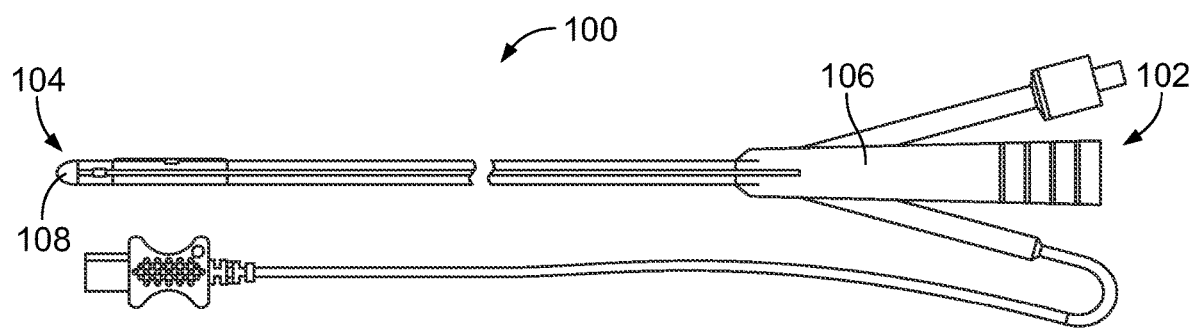
FIG. 1 is a perspective view of a catheter assembly in accordance with an exemplary embodiment.

FIG. 1 is a perspective view of a catheter assembly 100 in accordance with an exemplary embodiment. The catheter assembly 100 extends between a proximal end 102 and a distal end 104. The catheter assembly 100 includes a handle 106 at the proximal end 102. The handle 106 may be used to actuate or manipulate the distal end 104 and/or one or more medical implements 108 at the distal end 104. For example, the catheter assembly 100 may be a steerable catheter assembly. The handle 106 may be rotated and/or translated to actuate or manipulate the distal end 104, such as using pull wires, springs, or other types of actuation elements extending between the handle 106 and the distal end 104. In various embodiments, the medical implement 108 may be a stent and the catheter assembly 100 is used for positioning the stent within a patient's body. In other embodiments, the medical implement 108 may be an electrical device, such as a sensor, at the distal end 104. The electrical device may be electrically connected to a connector via one or more electrical wires, such as ECG wires, extending from the electrical device to the connector. Other types of medical implements may be provided in alternative embodiments.

Figure 2:
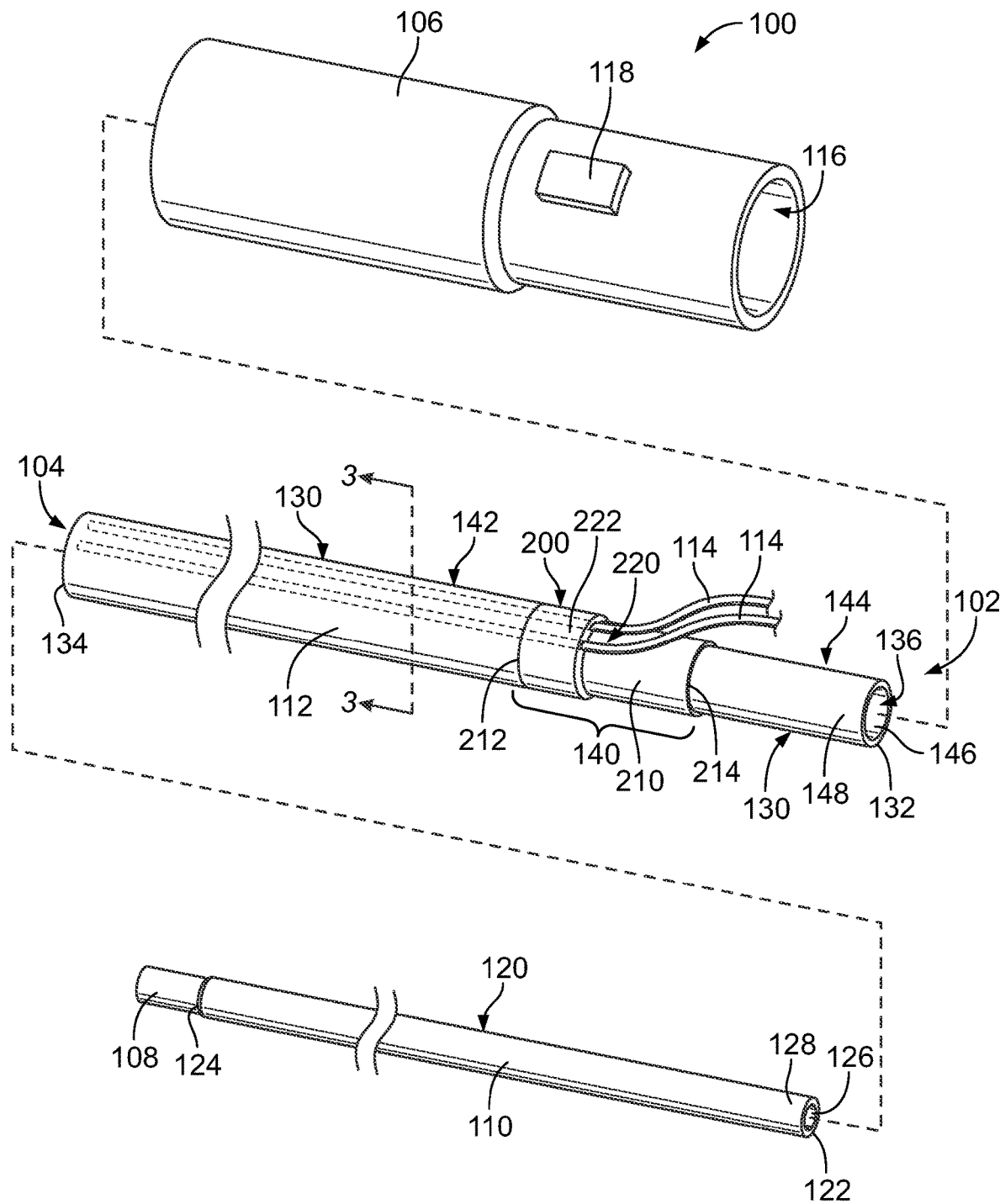
FIG. 2 is an exploded view of the catheter assembly in accordance with an exemplary embodiment.

FIG. 2 is an exploded view of the catheter assembly 100 in accordance with an exemplary embodiment. The catheter assembly 100 includes an inner shaft 110, an outer shaft 112, one or more catheter wires 114, and an exit path connector 200 for controlling the position of the catheter wires 114 along the outer shaft 112. In various embodiments, the catheter wires 114 may have a spring coil or sheath extending the length of the catheter wires 114 to protect the catheter wires 114. The inner shaft 110 is configured to be coaxially disposed within the outer shaft 112. The exit path connector 200 is used to route the catheter wires 114 from an interior to an exterior of the outer shaft 112. The exit path connector 200 provides side exit points for the catheter wires 114.

The handle 106 is configured to be coupled to the outer shaft 112 and the exit path connector 200 at the proximal end 102. In an exemplary embodiment, the handle 106 includes a handle bore 116 that receives the outer shaft 112 and the exit path connector 200. The handle 106 may be coupled to the inner shaft 110 to move the inner shaft 110 relative to the outer shaft 112. In various embodiments, the handle 106 includes one or more actuators 118, such as levers, to move the inner shaft 110 relative to the outer shaft 112. In various embodiments, the handle 106 is operably coupled to the catheter wires 114. For example, the catheter wires 114 may be pull wires, springs or other types of actuators coupled to the inner shaft 110 and/or the outer shaft 112 at the distal end 104 for actuating the distal end 104 of the catheter assembly 100. Other types of wires may be provided in alternative embodiments, such as electrical wires used to transmit data signals from the medical implement 108 to the proximal end 102 of the catheter assembly 100. The catheter wires 114 may be probe cables in other various embodiments.

The inner shaft 110 includes an inner shaft body 120 extending between a proximal end 122 and a distal end 124. In various embodiments, the medical implement 108 may be held by the inner shaft 110 at the distal end 124. In an exemplary embodiment, the inner shaft body 120 is a tubular member being hollow. In various embodiments, the inner shaft body 120 includes an inner layer 126 and an outer layer 128 surrounding the inner layer 126. The inner shaft body 120 may include multiple layers, such as multiple inner layers or multiple outer layers as a stackup of materials, that provide structural support, coverings, lubricious surfaces, and the like. The inner shaft body 120 may be flexible, such as for manipulation of the inner shaft 110 within the patient's body. For example, the inner layer 126 may be spiral cut or include a plurality of slots cut in the wall thereof to increase the flexibility of the inner layer 126. In other various embodiments, the inner layer 126 may be a braided inner layer, such as a stainless-steel wire mesh braid. Optionally, the inner layer 126 may be a hypodermic tube or hypotube. However, the inner layer 126 may be another type of structure in alternative embodiments. In various embodiments, the inner layer 126 is a structural layer providing structural support and provides the general shape of the inner shaft body 120, with the other layers, including the outer layer 128, being supported by the inner layer 126. The inner layer 126 may be a solid rod in various embodiments rather than a tubular structure. An inner coating layer may be applied to the interior surface of the inner layer 126, such as to form a lubricious surface. For example, the inner coating layer may be a PTFE liner, an FEP liner, or other various medical grade thermoplastic elastomer coatings.

In an exemplary embodiment, the outer layer 128 is manufactured from a polymer material having low frictional properties, such as a fluoropolymer material, a blend of fluoropolymer materials, a nylon material, a polyethylene material, and the like. The outer layer 128 may be manufactured from a material having good flex properties. In various embodiments, the outer layer 128 is a polymer jacket. In various embodiments, polymer layers may be provided along both the interior and exterior surfaces of the inner shaft 110. Optionally, the inner layer 126 may be used as a forming structure for forming the outer layer 128 and the inner layer 126 may be removed after the outer layer 128 is formed such that the inner shaft 110 includes only the outer layer 128. In various embodiments, the outer layer 128 may be spiral cut or include a plurality of slots cut in the wall thereof to increase the flexibility of the inner shaft 110.

The outer shaft 112 includes an outer shaft body 130 extending between a proximal end 132 and a distal end 134. The outer shaft body 130 forms an outer shaft bore 136 that receives the inner shaft 110. The inner shaft 110 may be movable relative to the outer shaft 112 within the outer shaft bore 136. For example, the inner shaft 110 may be moved axially relative to the outer shaft 112 and/or the inner shaft 110 may be rotated relative to the outer shaft 112. In an exemplary embodiment, the catheter wires 114 are routed within the outer shaft bore 136 between the distal end 134 and the exit path connector 200, such as in a space between the outer shaft body 130 and the inner shaft body 120. The exit path connector 200 transitions the catheter wires 114 through side exit ports between the interior of the outer shaft 112 and the exterior of the outer shaft 112, such as for connection to the handle 106 or other device.

In various embodiments, the outer shaft body 130 includes an inner layer 146 and an outer layer 148 surrounding the exterior of the inner layer 146. The outer shaft body 130 may include multiple layers, such as multiple inner layers or multiple outer layers as a stackup of materials, that provide structural support, coverings, lubricious surfaces, and the like. The outer shaft body 130 may be flexible, such as for manipulation of the outer shaft 112 within the patient's body. For example, the inner layer 146 may be spiral cut or include a plurality of slots cut in the wall thereof to increase the flexibility of the inner layer 146. In other various embodiments, the inner layer 146 may be a braided inner layer, such as a stainless-steel wire mesh braid. Optionally, the inner layer 146 may be a hypodermic tube or hypotube. However, the inner layer 146 may be another type of structure in alternative embodiments. In various embodiments, the inner layer 146 is a structural layer providing structural support and provides the general shape of the outer shaft body 130, with the other layers, including the outer layer 148, being supported by the inner layer 146. The inner layer 146 may be a solid rod in various embodiments rather than a tubular structure. An inner coating layer may be applied to the interior surface of the inner layer 146, such as to form a lubricious surface. For example, the inner coating layer may be a PTFE liner, an FEP liner, or other various medical grade thermoplastic elastomer coatings.

In an exemplary embodiment, the outer layer 148 is manufactured from a polymer material having low frictional properties, such as a fluoropolymer or a blend of fluoropolymers, a nylon material, and the like. The outer layer 148 may be manufactured from a material having good flex properties. In various embodiments, the outer layer 148 is a polymer jacket. In various embodiments, polymer layers may be provided along both the interior and exterior surfaces of the inner layer 146. Optionally, the inner layer 146 may be used as a forming structure for forming the outer layer 148 and the inner layer 146 may be removed after the outer layer 148 is formed such that the outer shaft 112 includes only the outer layer 148. In various embodiments, the outer layer 148 may be spiral cut or include a plurality of slots cut in the wall thereof to increase the flexibility of the outer shaft 112.

In an exemplary embodiment, the outer shaft 112 includes a wire transition section 140 proximate to the proximal end 132. The exit path connector 200 is coupled to the outer shaft body 130 at the wire transition section 140. For example, the exit path connector 200 is coupled to the inner layer 146 and/or coupled to the outer layer 148. The outer layer 148 may be formed in situ over the inner layer 146 and/or a portion of the exit path connector 200 to form a seamless transition across the inner layer 146 and the exit path connector 200. For example, the outer layer 148 may extend over and cover the seam between the inner layer 146 and the exit path connector 200 to add rigidity and structural strength at the interface of the outer shaft 112 and the exit path connector 200. In an exemplary embodiment, the exit path connector 200 is separate and discrete from the outer shaft body 130, being coupled to the outer shaft body 130 at the wire transition section 140. For example, the exit path connector 200 is separately manufactured from the outer shaft body 130 (for example, from the inner layer 146 of the outer shaft body 130 and from the outer layer 148 of the outer shaft body 130). When assembled, the exit path connector 200 forms part of or an extension of the outer shaft 112. For example, the outer shaft body 130 is discontinuous at the wire transition section 140 including a forward section 142 forward of the wire transition section 140 and a rearward section 144 rearward of the wire transition section 140. The exit path connector 200 is positioned between the forward section 142 and the rearward section 144. The exit path connector 200 connects the forward section 142 and the rearward section 144.

The exit path connector 200 includes a body section 210 extending between a front 212 and a rear 214. The body section 210 is hollow including an exit path connector bore 216 (shown in FIG. 4) between the front 212 and the rear 214. The exit path connector bore 216 receives the inner shaft 110. When the exit path connector 200 is coupled to the outer shaft body 130, the exit path connector bore 216 and the outer shaft bore 136 define a continuous bore that receives the inner shaft 110. The body section 210 includes one or more side exit ports 220 at a side 222 of the body section 210. The exit path connector 200 defines the exit path locations for the catheter wires 114 along the outer shaft 112 by controlling the location of the side exit ports 220 relative to the front 212 and the rear 214. The exit path connector 200 controls the exit path angle of the catheter wires 114 from the interior of the exit path connector 200 to the exterior of the exit path connector 200. For example, the size, shape, location, angle, and thickness of material of the body section 210 around the side exit ports 220 are repeatedly and reliably controlled. For example, the body section 210 may be manufactured using precision manufacturing processes, such as 3D printing, laser cutting, injection molding, machining and the like. In an exemplary embodiment, the handle 106 is coupled to the outer shaft 112 and the exit path connector 200 to cover the wire exit location.

Figure 3:
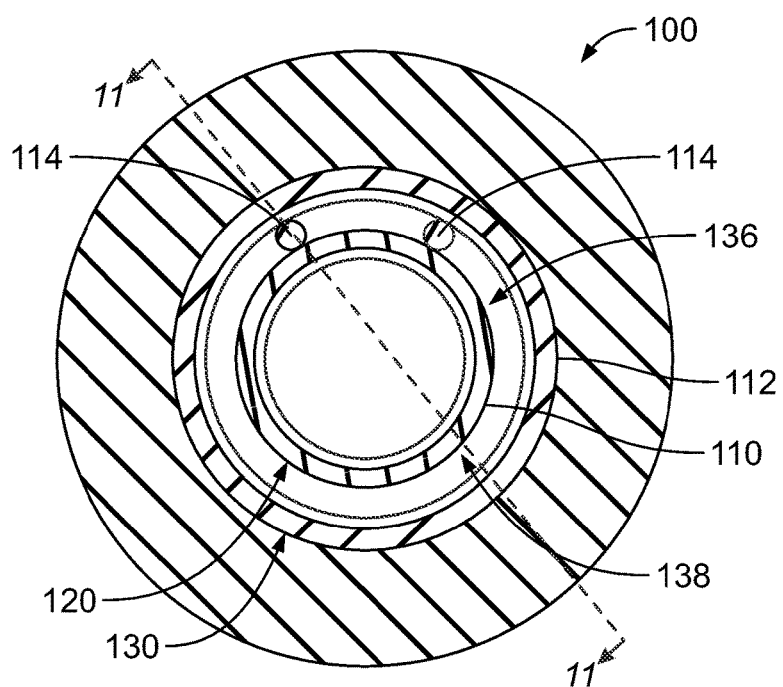
FIG. 3 is a cross-sectional view of the catheter assembly in accordance with an exemplary embodiment.

FIG. 3 is a cross-sectional view of the catheter assembly 100 in accordance with an exemplary embodiment. FIG. 3 illustrates the inner shaft 110 within the outer shaft bore 136 of the outer shaft 112. The catheter wires 114 are routed in a gap 138 between the outer shaft body 130 and the inner shaft body 120. Optionally, the catheter wires 114 may be coupled to the inner shaft body 120 and/or the outer shaft body 130 to flex or bend the inner shaft 110 and/or the outer shaft 112 for steering the catheter assembly 100 within the patient's body.

Figure 4:
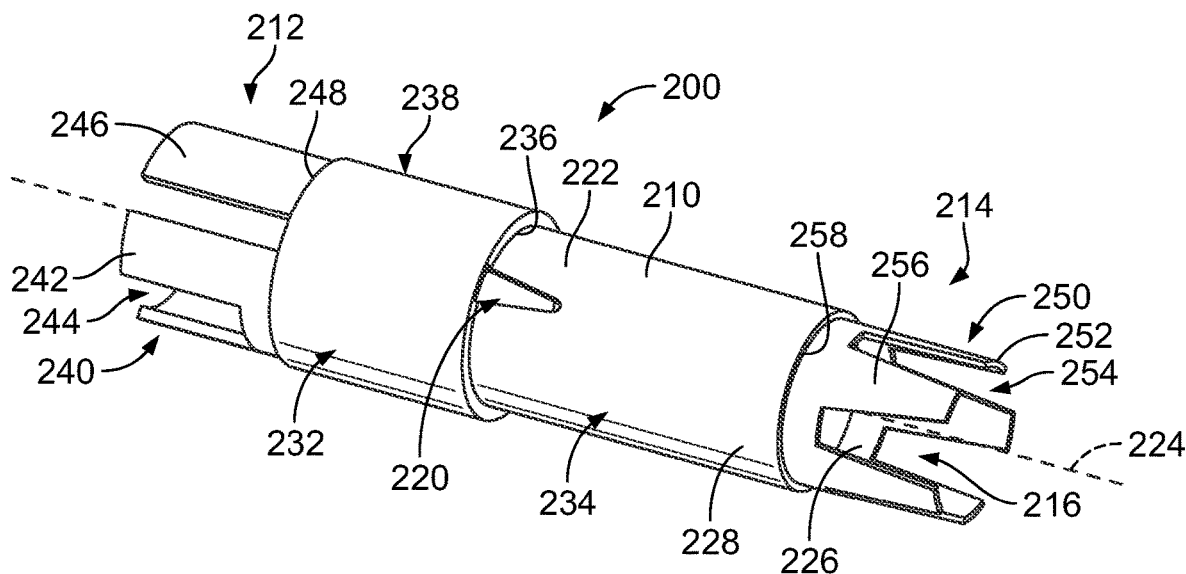
FIG. 4 is a perspective view of an exit path connector of the catheter assembly in accordance with an exemplary embodiment.
Figure 5:
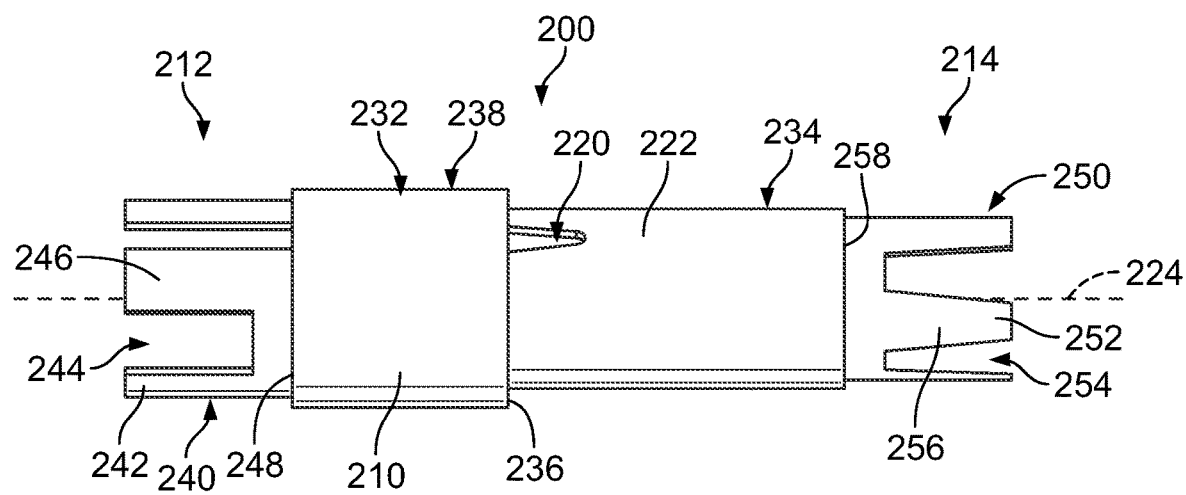
FIG. 5 is a side view of the exit path connector in accordance with an exemplary embodiment.
Figure 6:
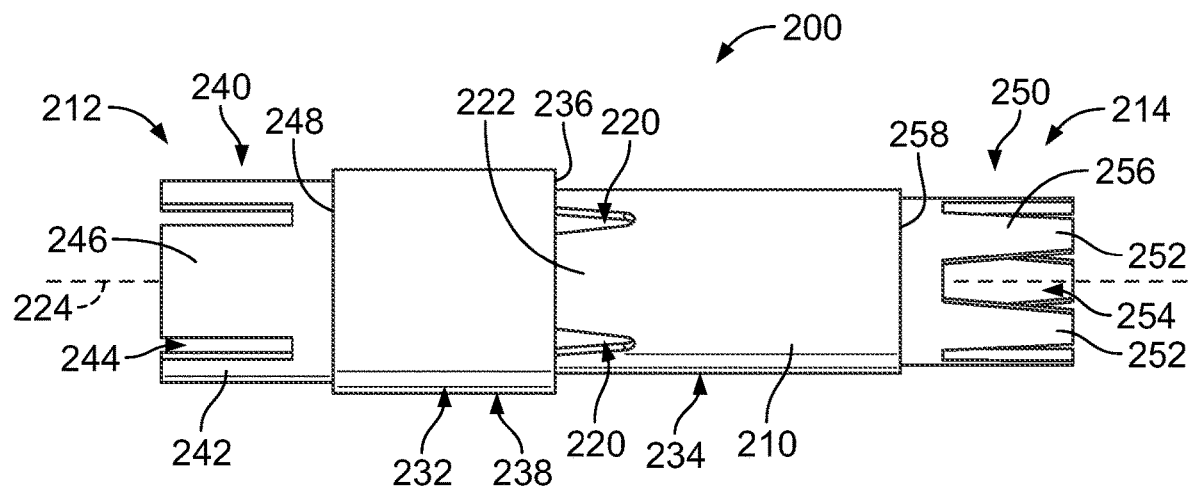
FIG. 6 is a top view of the exit path connector in accordance with an exemplary embodiment.
Figure 7:
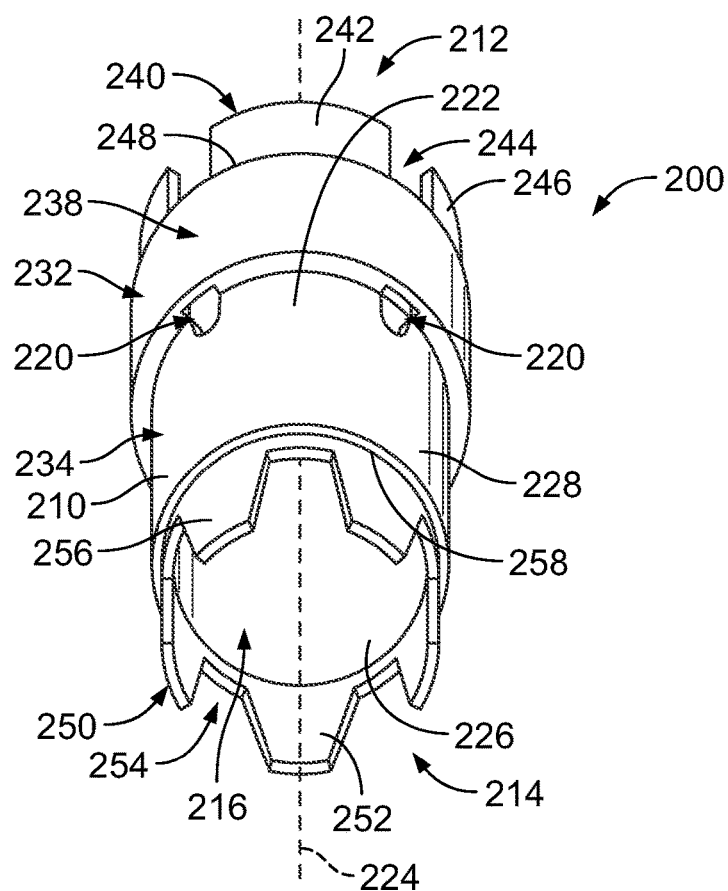
FIG. 7 is a rear perspective view of the exit path connector in accordance with an exemplary embodiment.

FIG. 4 is a perspective view of the exit path connector 200 in accordance with an exemplary embodiment. FIG. 5 is a side view of the exit path connector 200 in accordance with an exemplary embodiment. FIG. 6 is a top view of the exit path connector 200 in accordance with an exemplary embodiment. FIG. 7 is a rear perspective view of the exit path connector 200 in accordance with an exemplary embodiment.

The exit path connector 200 includes the body section 210 extending between the front 212 and the rear 214. The front 212 is configured to face the distal end of the catheter assembly 100 and the rear 214 is configured to face the proximal end 102 of the catheter assembly 100. In an exemplary embodiment, the body section 210 is rigid and retains shape during assembly and use. For example, the body section 210 may be manufactured from a metal material, such as a stainless-steel material. In other various embodiments, the body section 210 may be manufactured from a polymer material. Optionally, the polymer material may be a high temperature polymer material having a higher melting point than the outer layer 148 such that the body section 210 retains shape during application of the outer layer 148 to the exit path connector 200. The body section 210 may be manufactured by a 3D printing process. In other various embodiments, the body section 210 may be manufactured by a machining process. Optionally, the body section 210 may be processed after forming, such as being coated, plated or subject to other post-processing. The body section 210 is rigid to protect the catheter wires 114 and prevent damage or breakage at the wire exit points. The exit path connector forms a controlled connecting junction along the outer shaft 112 for connecting the catheter wires 114 to the handle 106 or other device.

The side exit ports 220 are arranged along the side 222 of the body section 210 between the front 212 and the rear 214. Any number of side exit ports 220 may be provided. In the illustrated embodiment, the exit path connector 200 includes two side exit ports 220 arranged at the top; however, greater or fewer side exit ports 220 may be provided and the side exit ports 220 may be at other locations in alternative embodiments. In various embodiments, the side exit ports 220 may be approximately centered between the front 212 and the rear 214. In alternative embodiments, the side exit ports 220 may be located closer to the front 212 or located closer to the rear 214. In other alternative embodiments, the side exit ports 220 may be located at different axial positions along the side 222 of the body section 210. The side exit ports 220 may be at a predetermined distance from the front 212 and/or the rear 214 for controlled location of the exit points for the catheter wires 114. The side exit ports 220 extend at an angle transverse to a bore axis 224 of the exit path connector bore 216. The side exit ports 220 extend between an inner surface 226 of the body section 210 and an outer surface 228 of the body section 210. The side exit ports 220 define openings to allow the catheter wires 114 to extend from the interior of the exit path connector 200 to the exterior of the exit path connector 200. The side exit ports 220 have a controlled entrance and exit for the catheter wires 114.

The body section 210 includes a front hub 232 at the front 212 and a rear hub 234 at the rear 214. In an exemplary embodiment, a shoulder 236 is formed between the front hub 232 and the rear hub 234. In an exemplary embodiment, the shoulder 236 forms a handle mount 238 for coupling the handle 106 (shown in FIG. 2) to the exit path connector 200. For example, the handle mount 238 includes one or more handle locating surfaces for locating the handle 106 relative to the exit path connector 200. For example, the handle 106 may engage the rear facing surface of the shoulder 236 to axially locate the handle 106 relative to the exit path connector 200.

In an exemplary embodiment, the front hub 232 has a larger outer diameter than the rear hub 234. Optionally, the front hub 232 may have a larger inner diameter than the rear hub 234. Optionally, the body section 210 may be thicker along the front hub 232 compared to the rear hub 234. However, in alternative embodiments, the rear hub 234 may have a larger diameter than the front hub 232. In other various embodiments, the front hub 232 and the rear hub 234 may have the same diameters. Optionally, in such embodiments, a flange or rim may extend outward from the front hub 232 and/or the rear hub 234, such as to form the handle mount. In other various embodiments, the front hub 232 and/or the rear hub 234 may have a non-continuous diameter, such as being tapered. In an exemplary embodiment, the side exit ports 220 are provided at the transition between the front hub 232 and the rear hub 234. For example, the side exit ports 220 pass through the shoulder 236. The catheter wires 114 are configured to be routed interior of the front hub 232 and exterior of the rear hub 234. In an exemplary embodiment, the front hub 232 has an increased inner diameter for routing the catheter wires 114 along the interior of the front hub 232 and the rear hub 234 has a reduced outer diameter for routing the catheter wires 114 along the exterior of the rear hub 234. In an exemplary embodiment, the front hub 232 has an increased thickness to provide sufficient material around the side exit ports 220 to reduce breakage of the exit port connector 200 at the side exit ports 220. In alternative embodiments, the body section 210 may be a multi-piece body having the front hub 232 separate from the rear hub 234 and coupled thereto.

In an exemplary embodiment, the exit path connector 200 includes a front joining section 240 extending forward of the body section 210 at the front 212. The front joining section 240 includes front joining features 242 and front openings 244 between the front joining features 242. The front openings 244 are located between the front joining features 242. In the illustrated embodiment, the front openings 244 are open at the front. In various embodiments, the front joining features 242 may be thinner than the front hub 232 between the inner surface 226 and the outer surface 228. For example, the front joining features 242 may be stepped radially inward to provide a circumferential space for receiving the outer layer 148 (shown in FIG. 2) when the exit path connector 200 is joined to the outer shaft 112 (shown in FIG. 2). The radial step forms a front shoulder 248 between the front hub 232 and the front joining section 240. In the illustrated embodiment, the front joining features 242 are lap joints 246 cantilevered from the front 212. The lap joints 246 may be wedge shaped tabs being thinner at the outer edges of the lap joints 246 and being thicker at the bases of the lap joints 246 where the lap joints 246 extend from the front hub 232. The lap joints 246 may be trapezoidal shaped in various embodiments. The front joining features 242 and/or the front openings 244 may have other shapes in alternative embodiments.

In an exemplary embodiment, the exit path connector 200 includes a rear joining section 250 extending forward of the body section 210 at the rear 214. The rear joining section 250 includes rear joining features 252 and rear openings 254 between the rear joining features 252. The rear openings 254 are located between the rear joining features 252. In the illustrated embodiment, the rear openings 254 are open at the rear. In various embodiments, the rear joining features 252 may be thinner than the rear hub 234 between the inner surface 226 and the outer surface 228. For example, the rear joining features 252 may be stepped radially inward to provide a circumferential space for receiving the outer layer 148 (shown in FIG. 2) when the exit path connector 200 is joined to the outer shaft 112 (shown in FIG. 2). The radial step forms a rear shoulder 258 between the rear hub 234 and the rear joining section 250. In the illustrated embodiment, the rear joining features 252 are lap joints 256 cantilevered from the rear 214. The lap joints 256 may be wedge shaped tabs being thinner at the outer edges of the lap joints 256 and being thicker at the bases of the lap joints 256 where the lap joints 256 extend from the rear hub 234. The lap joints 256 may be trapezoidal shaped in various embodiments. The rear joining features 252 and/or the rear openings 254 may have other shapes in alternative embodiments.

Figure 8:
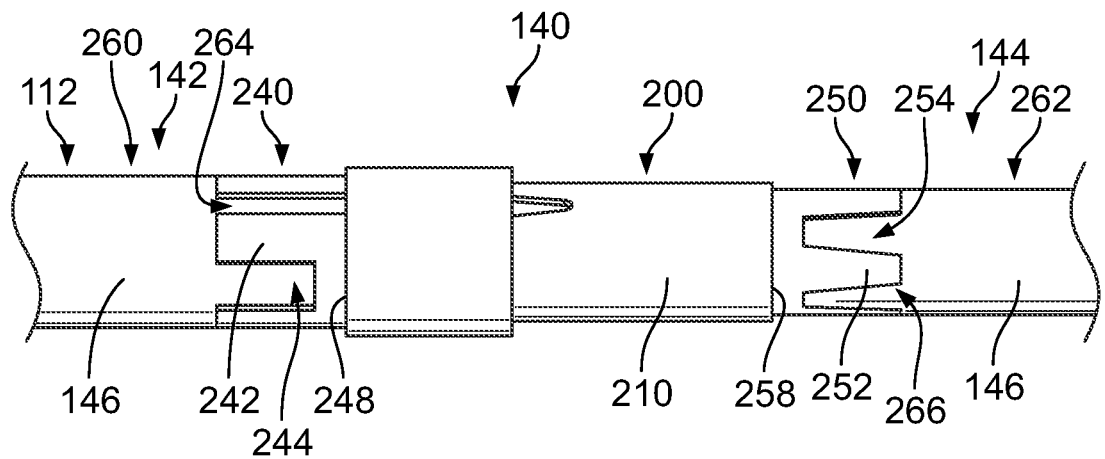
FIG. 8 is a side view of an outer shaft of the catheter assembly in a partially assembled state.
Figure 9:
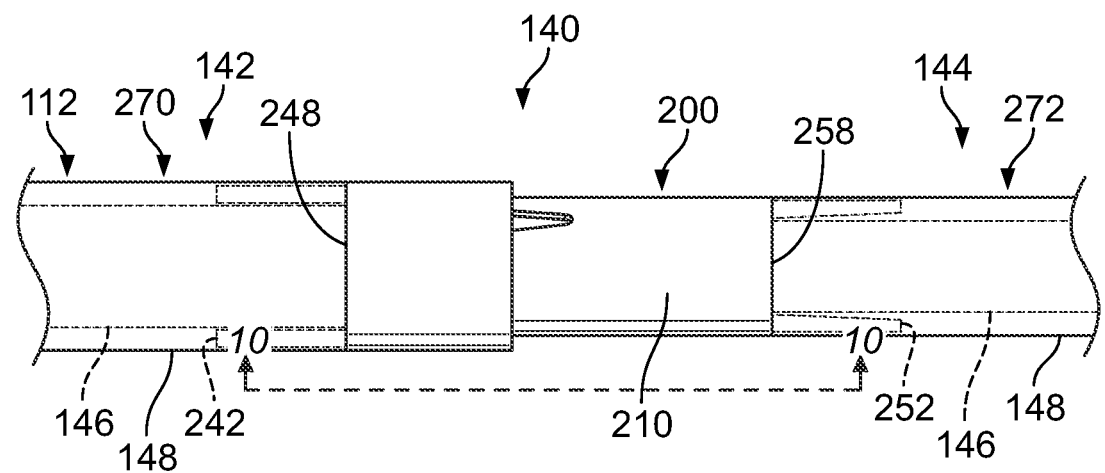
FIG. 9 is a side view of the outer shaft in an assembled state.

FIG. 8 is a side view of the outer shaft 112 in a partially assembled state. FIG. 9 is a side view of the outer shaft 112 in an assembled state. The exit path connector 200 is positioned at the wire transition section 140 of the outer shaft 112 between the forward section 142 and the rearward section 144. However, in alternative embodiments, the outer shaft 112 may be provided without the rearward section 144, instead having the exit path connector 200 positioned rearward of the forward section 142.

During assembly, the exit path connector 200 is coupled to the inner layer 146 (FIG. 8) of the outer shaft 112. The front joining section 240 is coupled to the forward section 142 of the inner layer 146 and the rear joining section 250 is coupled to the rearward section 144 of the inner layer 146. In an exemplary embodiment, the inner layer 146 is discontinuous with the body section 210 of the exit path connector 200 between forward and rearward sections 260, 262 of the outer layer 148. The front joining features 242 are coupled to the inner layer 146 at a front seam 264. For example, the front joining features 242 may engage the exterior surface of the inner layer 146. A portion of the inner layer 146 extends into the exit path connector bore 216 at the front joining section 240. The inner layer 146 is exposed through the front openings 244. The rear joining features 252 are coupled to the inner layer 146 at a rear seam 266. For example, the rear joining features 252 may engage the exterior surface of the inner layer 146. A portion of the inner layer 146 extends into the exit path connector bore 216 at the rear joining section 250. The inner layer 146 is exposed through the rear openings 254.

During assembly, the outer layer 148 (FIG. 9) is coupled to the inner layer 146 and the exit path connector 200. For example, the outer layer 148 may be applied in situ after the exit path connector 200 is coupled to the inner layer 146. In an exemplary embodiment, the outer layer 148 is a heat shrink tubing applied to the exit path connector 200 and the inner layer 146. In other various embodiments, the outer layer 148 is an overmold material that is molded in situ over portions of the exit path connector 200 and the inner layer 146. The outer layer 148 may be applied by other processes in alternative embodiments, such as chemical bonding.

The outer layer 148 surrounds the exterior of the inner layer 146 and surrounds the exterior of the front and rear joining sections 240, 250. The outer layer 148 is seamlessly coupled to the inner layer 146 and the front and rear joining sections 240, 250. For example, the outer layer 148 covers and forms a seamless transition across the front seam 264 and the rear seam 266. In an exemplary embodiment, the outer layer 148 is discontinuous with the body section 210 of the exit path connector 200 between forward and rearward sections 270, 272 of the outer layer 148. The forward section 270 of the outer layer 148 covers the forward section 260 of the inner layer 146 and the front joining section 240. The forward section 270 of the outer layer 148 is coupled to the front joining features 242. The forward section 270 of the outer layer 148 extends into the front openings 244. The forward section 270 of the outer layer 148 engages the front shoulder 248. The rearward section 272 of the outer layer 148 covers the rearward section 262 of the inner layer 146 and the rear joining section 250. The rearward section 272 of the outer layer 148 is coupled to the rear joining features 252. The rearward section 272 of the outer layer 148 extends into the rear openings 254. The rearward section 272 of the outer layer 148 engages the rear shoulder 258. The outer layer 148 secures the exit path connector 200 to the inner layer 146.

Figure 10:
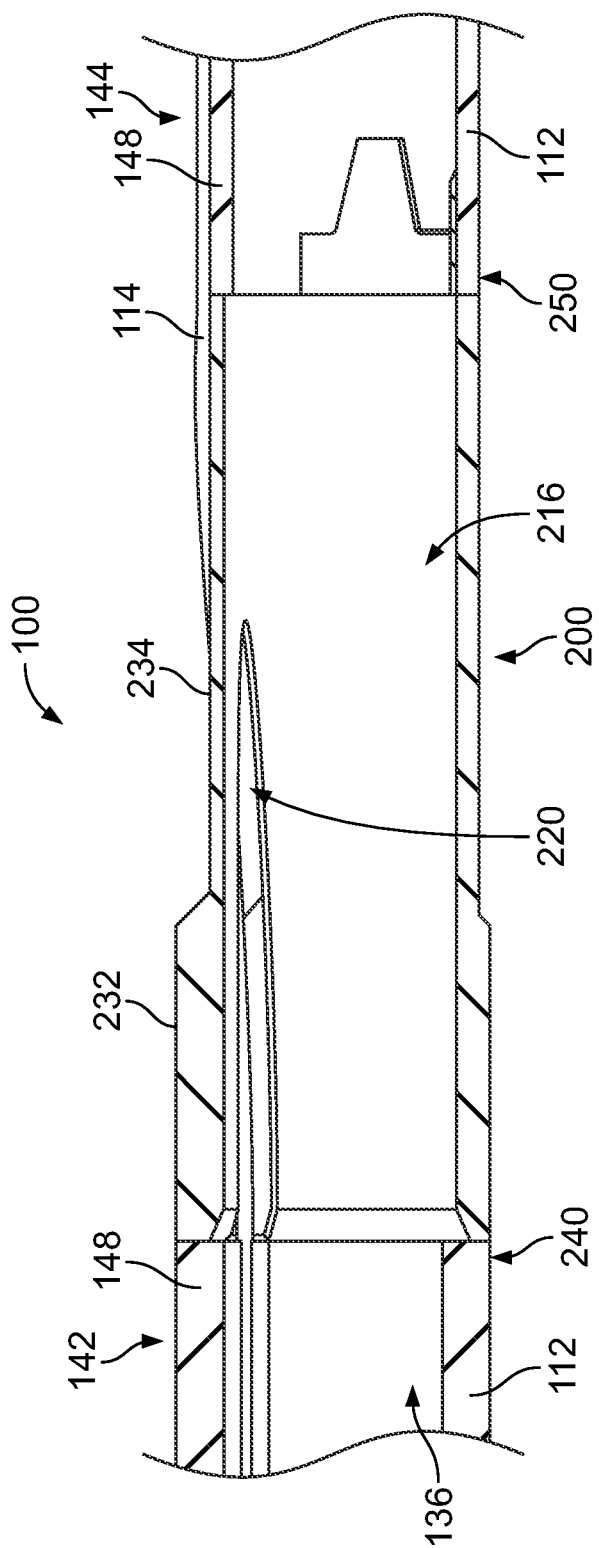
FIG. 10 is a cross-sectional view of a portion of the catheter assembly in accordance with an exemplary embodiment.

FIG. 10 is a cross-sectional view of a portion of the catheter assembly 100 in accordance with an exemplary embodiment showing the exit path connector 200 and a portion of the outer shaft 112. The exit path connector 200 is positioned between the forward section 142 and the rearward section 144. The catheter wires 114 extend through the outer shaft 112 and the exit path connector 200 to the side exit ports 220. The outer layer 148 is coupled to the exit path connector 200 at the front joining section 240 and the rear joining section 250. The catheter wires 114 extend through the interior of the outer shaft 112 (for example, within the outer shaft bore 136) along the forward section 142 of the outer shaft 112 and extend through the interior of the front hub 232 (for example, within the exit path connector bore 216) of the exit path connector 200. The catheter wires 114 extend through the side exit ports 220 to the exterior of the exit path connector 200. The catheter wires 114 extend along the exterior of the rear hub 234 and may extend along the exterior of the rearward section 144 of the outer shaft 112.

FIG. 11 is a cross-sectional view of a portion of the catheter assembly 100 in accordance with an exemplary embodiment. The exit path connector 200 is positioned at the wire transition section 140 of the outer shaft 112 between the forward section 142 and the rearward section 144. The handle 106 is coupled to the outer shaft 112 and/or the exit path connector 200. For example, the handle 106 may engage the outer surface 228 of the body section 210. The handle 106 may be positioned along the outer shaft 112 and the exit path connector 200 by engagement with the handle mount 238.

During assembly, the exit path connector 200 is coupled to the inner layer 146 of the outer shaft 112 and the outer layer 148 is coupled to the exit path connector 200 and the outer shaft 112. The front joining section 240 is coupled to the inner layer 146 and the outer layer 148 at the forward section 142 and the rear joining section 250 is coupled to the inner layer 146 and the outer layer 148 at the rearward section 144. Optionally, the front and rear joining features 242, 252 are located between the inner layer 146 and the outer layer 148. The outer layer 148 is formed around the front and rear joining features 242, 252, such as in the front and rear openings 244, 254.

In an exemplary embodiment, the exit path connector bore 216 and the outer shaft bore 136 are aligned along the bore axis 224. The inner shaft 110 is received in the outer shaft bore 136 and the exit path connector bore 216. The gap 138 is defined between the inner shaft body 120 and the outer shaft body 130. The gap 138 is also defined between the inner shaft body 120 and the body section 210 of the exit path connector 200. In an exemplary embodiment, the catheter wires 114 are routed through the catheter assembly 100 within the gap 138 to the side exit ports 220 in the exit path connector 200. The catheter wires 114 extend through the interior of the outer shaft 112 (for example, within the outer shaft bore 136) along the forward section 142 of the outer shaft 112 and extend through the interior of the front hub 232 (for example, within the exit path connector bore 216) of the exit path connector 200. The catheter wires 114 extend through the side exit ports 220 to the exterior of the exit path connector 200. For example, the catheter wires 114 extend along the exterior of the rear hub 234 and may extend along the exterior of the rearward section 144 of the outer shaft 112. The catheter wires 114 may be coupled to the handle 106 or another device at the exterior of the outer shaft 112 and/or at the exterior of the exit path connector 200.

FIG. 12 is a cross-sectional view of a portion of the catheter assembly 100 in accordance with an exemplary embodiment taken through the front hub 232 of the exit path connector 200 forward of the side exit ports 220. The inner shaft 110 is positioned in the exit path connector bore 216 with the gap 138 between the inner shaft body 120 and the body section 210 of the exit path connector 200. The catheter wires 114 are routed through the catheter assembly 100 within the gap 138.

FIG. 13 is a cross-sectional view of a portion of the catheter assembly 100 in accordance with an exemplary embodiment taken through the rear hub 234 of the exit path connector 200 rearward of the side exit ports 220. The catheter wires 114 extend through the side exit ports 220 to the exterior of the exit path connector 200. The catheter wires 114 extend along the exterior of the rear hub 234.

Figure 14:
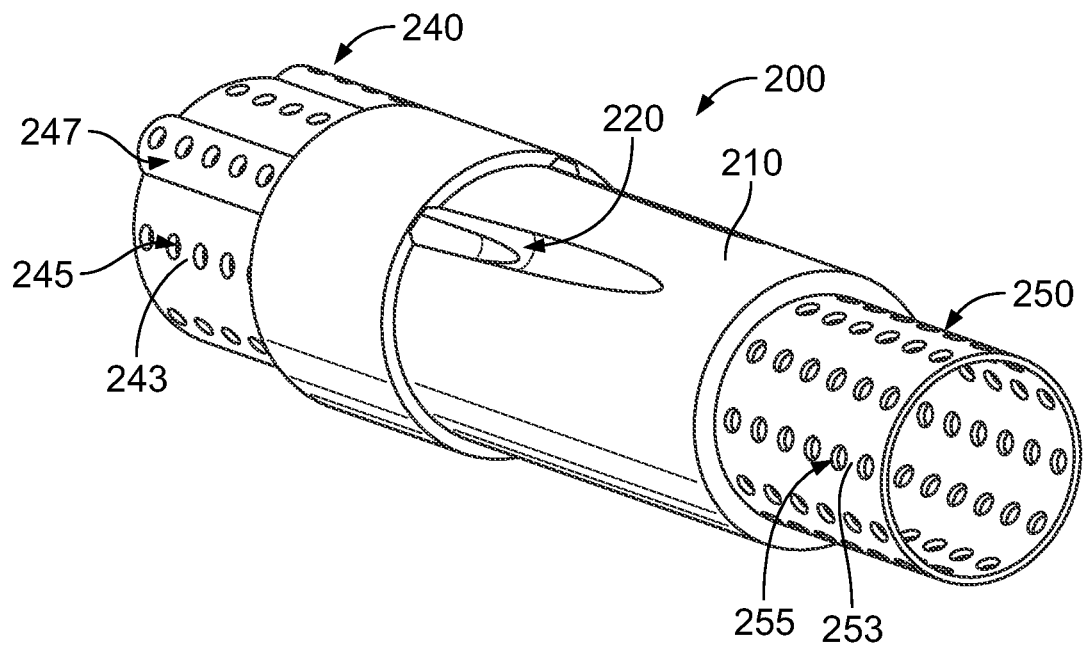
FIG. 14 is a perspective view of the exit path connector in accordance with an exemplary embodiment.

FIG. 14 is a perspective view of the exit path connector 200 in accordance with an exemplary embodiment. The exit path connector 200 includes the body section 210 and the side exit ports 220. In the illustrated embodiment, the exit path connector 200 includes perforated openings 245 at the front joining section 240 and perforated openings 255 at the rear joining section 250. In the illustrated embodiment, the perforated openings 245, 255 are circular; however, the perforated openings 245, 255 may have other shapes, such as being oval, rectangular, arcuate, or other shape. The perforated openings 245, 255 may be elongated, such as being elongated parallel to the axis of the exit path connector 200, perpendicular to the axis of the exit path connector 200 or elongated in other directions. In various embodiments, the front joining section 240 includes hoods 247 that receive the catheter wires 114. The front and rear joining sections 240, 250 are shaped differently in the illustrated embodiment, compared to the embodiment illustrated in FIG. 4. The perforated openings 245, 255 are separated by webbings 243, 253 at the front and rear joining sections 240, 250. The outer layer 148 (shown in FIG. 9) may cover the webbings 243, 253 and fill the perforated openings 245, 255. The webbings 243, 253 are configured to be coupled to the inner layer 146 (shown in FIG. 8).

Figure 15:
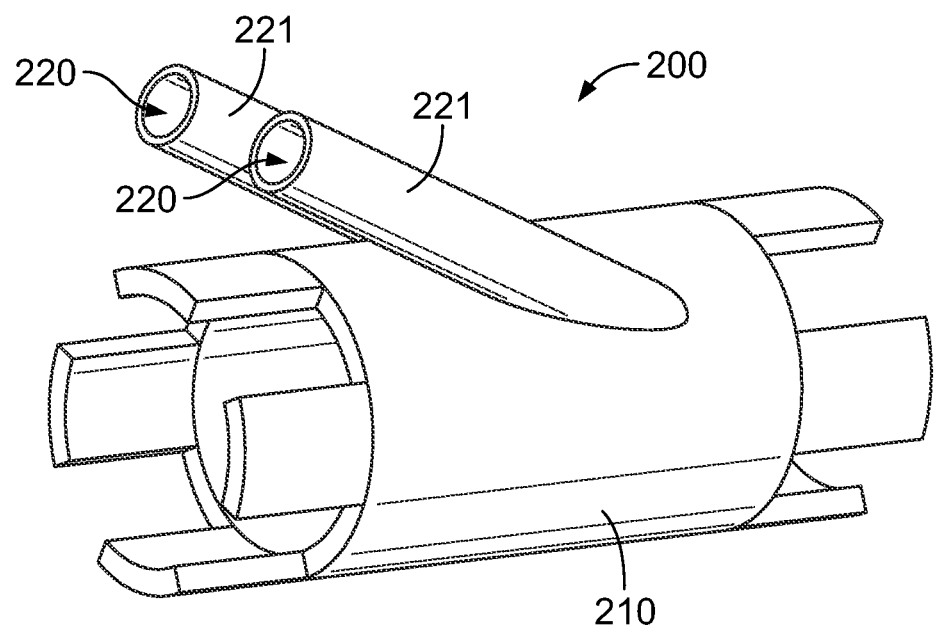
FIG. 15 is a perspective view of the exit path connector in accordance with an exemplary embodiment.

FIG. 15 is a perspective view of the exit path connector 200 in accordance with an exemplary embodiment. The exit path connector 200 includes the body section 210 and the side exit ports 220. In the illustrated embodiment, the side exit ports 220 are formed by exit tubes 221 extending from the body section 210. The outer layer 148 (shown in FIG. 9) may be applied to the body section 210 to cover the entire body section 210 with the exit tubes 221 extending through the outer layer 148. The front and rear joining sections 240, 250 may be coupled to the outer layer 148 and the inner layer 146 (shown in FIG. 8).

Figure 16:
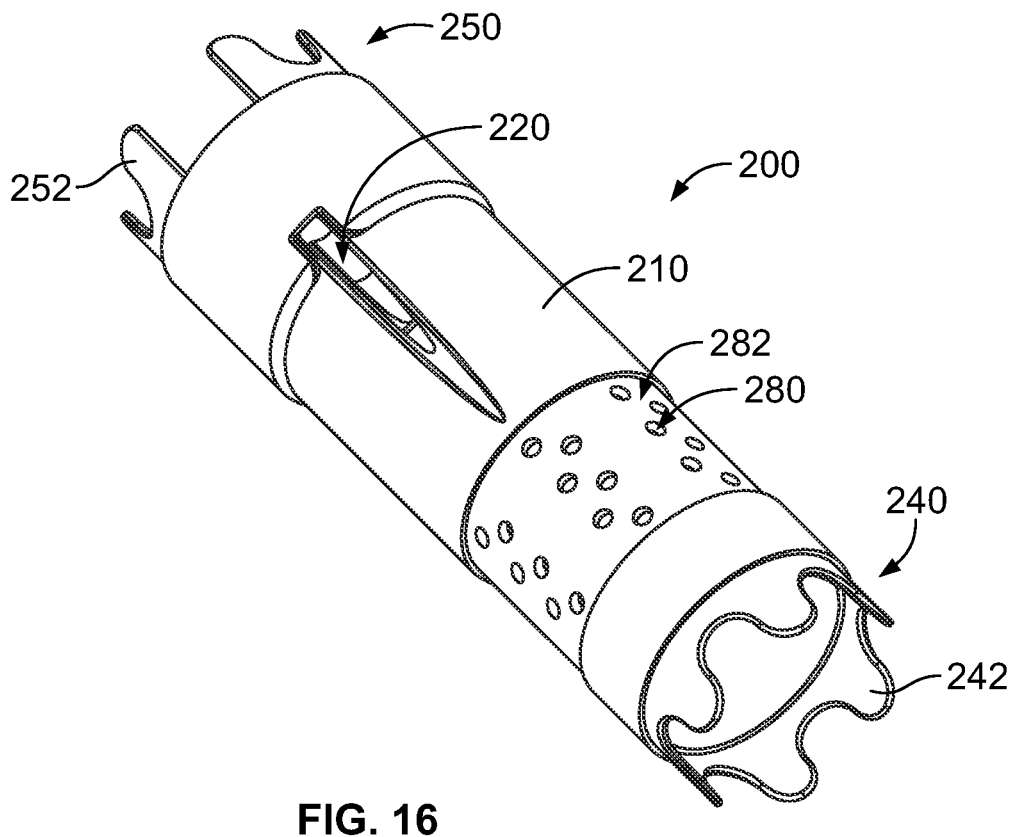
FIG. 16 is a front perspective view of the exit path connector in accordance with an exemplary embodiment.
Figure 17:
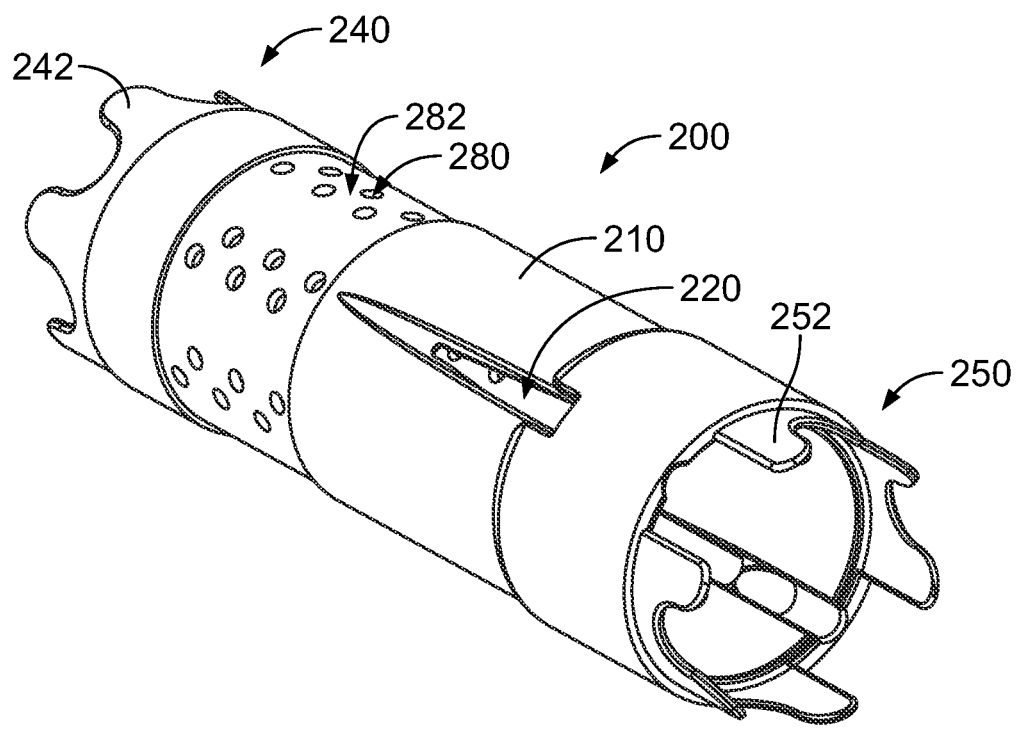
FIG. 17 is a rear perspective view of the exit path connector shown in FIG. 16 in accordance with an exemplary embodiment.

FIG. 16 is a front perspective view of the exit path connector 200 in accordance with an exemplary embodiment. FIG. 17 is a rear perspective view of the exit path connector 200 shown in FIG. 16 in accordance with an exemplary embodiment. The exit path connector 200 includes the body section 210 and the side exit ports 220. The body section 210 includes the front joining features 242 at the front joining section 240 and the rear joining features 252 at the rear joining section 250. The front and rear joining features 242, 252 include curved distal edges.

In the illustrated embodiment, the exit path connector 200 includes perforated openings 280 along an intermediate portion of the body section 210, which is remote from the front joining section 240 and remote from the rear joining section 250. In the illustrated embodiment, the perforated openings 280 are circular; however, the perforated openings 280 may have other shapes, such as being oval, rectangular, arcuate, or other shape. The perforated openings 280 may be elongated in alternative embodiments. The perforated openings 280 are separated by webbings 282. The outer layer 148 (shown in FIG. 9) may cover the webbings 282 and fill the perforated openings 280. The webbings 282 are configured to be coupled to the inner layer 146 (shown in FIG. 8).

Figure 18:
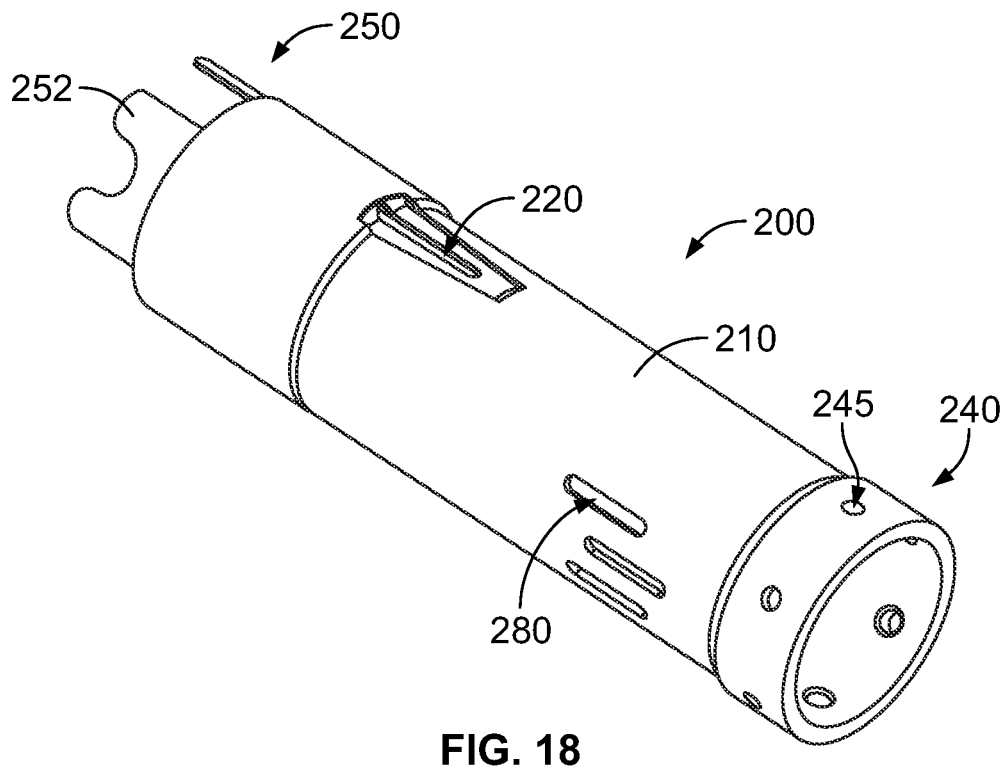
FIG. 18 is a front perspective view of the exit path connector in accordance with an exemplary embodiment.
Figure 19:
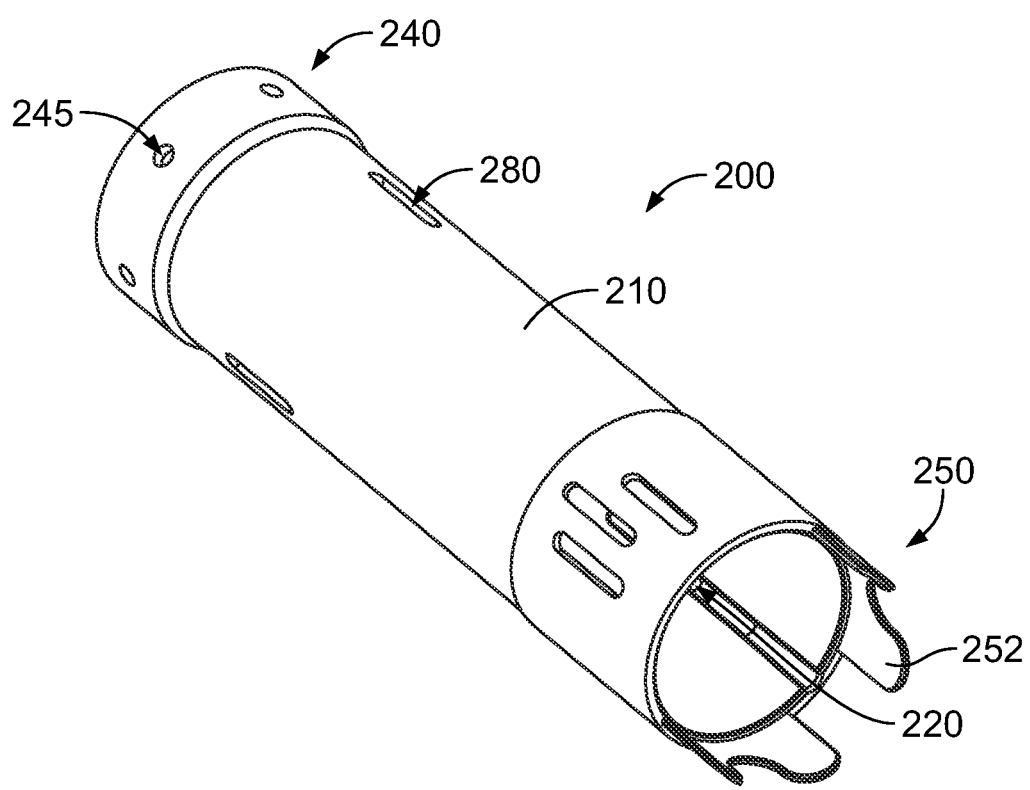
FIG. 19 is a rear perspective view of the exit path connector shown in FIG. 18 in accordance with an exemplary embodiment.

FIG. 18 is a front perspective view of the exit path connector 200 in accordance with an exemplary embodiment. FIG. 19 is a rear perspective view of the exit path connector 200 shown in FIG. 18 in accordance with an exemplary embodiment. The exit path connector 200 includes the body section 210 and the side exit ports 220. The body section 210 includes the rear joining features 252 at the rear joining section 250. The body section 210 includes the front perforated openings 245 at the front joining section 240. The body section further includes the intermediate perforated openings 280 along the intermediate portion of the body section 210. In the illustrated embodiment, the perforated openings 280 are elongated openings, such as being oval shaped. The perforated openings 280 may have other shapes in alternative embodiments. In the illustrated embodiment, the perforated openings 280 are elongated parallel to the axis of the body section 210; however, the perforated openings 280 may be perpendicular to the axis or transverse to the axis in alternative embodiments. The inner layer 146 (shown in FIG. 8) may fill the front perforated openings 245 and/or the intermediate perforated openings 280.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A catheter assembly comprising:
   an inner shaft extending between a proximal end and a distal end;
   an outer shaft having an outer shaft body forming an outer shaft bore, the outer shaft bore receiving the inner shaft, the outer shaft extending between a proximal end and a distal end, the outer shaft having a wire transition section proximate to the proximal end, the outer shaft being discontinuous at the wire transition section, the wire transition section including a forward section and a rearward section;
   an exit path connector coupled to the outer shaft body at the wire transition section, the exit path connector being positioned between and connecting the forward section and the rearward section, the exit path connector having a rigid body section separate and discrete from the outer shaft body and coupled to the outer shaft body, the body section defining an exit path connector bore that receives the inner shaft, the body section having a side exit port at a side of the body section, the side exit port being open to the exit path connector bore; and,
   a catheter wire extending between the distal end and the proximal end of the outer shaft, the catheter wire passing through the side exit port from an interior of the exit path connector to an exterior of the exit path connector, the catheter wire extending within the outer shaft bore from the exit path connector to the distal end of the outer shaft.

2. The catheter assembly of claim 1, wherein the body section of the exit path connector is manufactured from a different material than a material of the outer shaft body.

3. The catheter assembly of claim 1, wherein the outer shaft includes an inner layer defining the outer shaft bore, the exit path connector being coupled to the inner layer at a seam, the outer shaft including an outer layer on the inner layer and the exit path connector at the seam.

4. The catheter assembly of claim 1, wherein the outer shaft includes a hypotube defining the outer shaft bore, the exit path connector being coupled to the hypotube at a seam, the outer shaft including a polymer jacket formed in situ around the hypotube and the exit path connector at the seam.

5. The catheter assembly of claim 1, wherein the exit path connector includes a front joining section extending forward of the body section, the front joining section being coupled to the outer shaft body.

6. The catheter assembly of claim 5, wherein the exit path connector includes a rear joining section extending rearward of the body section, the rear joining section being coupled to the outer shaft body.

7. The catheter assembly of claim 5, wherein the front joining section includes lap joints coupled to the outer shaft.

8. The catheter assembly of claim 5, wherein the outer shaft includes an inner layer defining the outer shaft bore and an outer layer surrounding an exterior of the inner layer, the front joining section coupled to the inner layer at a seam, the outer layer being seamlessly coupled to the inner layer and the front joining section to cover the seam between the front joining section and the inner layer.

9. The catheter assembly of claim 1, wherein the body section includes an inner surface and an outer surface, the inner surface defining the exit path connector bore, the side exit port extending between the inner surface and the outer surface at an angle transverse to a bore axis of the exit path connector bore.

10. The catheter assembly of claim 1, further comprising a handle coupled to the outer shaft at the proximal end, the handle having a handle bore that receives the proximal end of the outer shaft and the exit path connector, the catheter wire exiting the side exit port into the handle bore.

11. The catheter assembly of claim 10, wherein the exit path connector includes a handle mount, the handle coupled to the handle mount of the exit path connector.

12. The catheter assembly of claim 1, wherein the body section of the exit path connector is stainless steel.

13. The catheter assembly of claim 1, wherein the body section of the exit path connector is a 3D printed body section.

14. The catheter assembly of claim 1, wherein the exit path connector extends between a front and a rear, the side exit port being positioned a predetermined distance from the front, the side exit port extending at a predetermined angle relative to a bore axis of the exit path connector bore.

15. The catheter assembly of claim 1, wherein the body section of the exit path connector includes a front hub and a rear hub, the front hub having a larger diameter than the rear hub, a shoulder formed between the front hub and the rear hub, the side exit port passing through the shoulder.

16. The catheter assembly of claim 15, wherein the front hub is thicker than the rear hub.

17. The catheter assembly of claim 1, wherein the side exit port is a first side exit port, the exit path connector including a second side exit port receiving a second catheter wire.

18. The catheter assembly of claim 1, wherein the catheter wire is a pull wire used to actuate at least one of the distal end of the inner shaft or the distal end of the outer shaft.

19. The catheter assembly of claim 1, further comprising a wire lumen receiving the catheter wire, the wire lumen passing through the side exit port.

20. A catheter assembly comprising:
an inner shaft extending between a proximal end and a distal end;
an outer shaft having an outer shaft body forming an outer shaft bore, the outer shaft bore receiving the inner shaft, the outer shaft extending between a proximal end and a distal end, the outer shaft having a wire transition section proximate to the proximal end, the outer shaft being discontinuous at the wire transition section, the wire transition section including a forward section and a rearward section;
an exit path connector coupled to the outer shaft body at the wire transition section, the exit path connector being positioned between and connecting the forward section and the rearward section, the exit path connector having a front joining section, a rear joining section, and a body section between the front joining section and the rear joining section, the exit path connector is separate and discrete from the outer shaft body, the front joining section being coupled to the outer shaft body, the rear joining section being coupled to the outer shaft body, the body section having an inner surface and an outer surface, the inner surface defining an exit path connector bore extending along a bore axis, the exit path connector bore receiving the inner shaft, the body section having a side exit port at a side of the body section, the side exit port extending between the inner surface and the outer surface at an angle transverse to the bore axis; and
a catheter wire extending between the distal end and the proximal end of the outer shaft, the catheter wire passing through the side exit port, the catheter wire passing along the inner surface of the body section forward of the side exit port, the catheter wire passing along the outer surface of the body section rearward of the side exit port, the catheter wire extending within the outer shaft bore from the exit path connector to the distal end of the outer shaft.

21. The catheter assembly of claim 20, wherein the outer shaft includes a hypotube defining the outer shaft bore, the exit path connector being coupled to the hypotube at a seam, the outer shaft including a polymer jacket formed in situ around the hypotube and the exit path connector at the seam.

22. The catheter assembly of claim 20, wherein the body section of the exit path connector includes a front hub and a rear hub, the front hub having a larger diameter than the rear hub, a shoulder formed between the front hub and the rear hub, the side exit port passing through the shoulder.

23. A catheter assembly comprising:
an inner shaft extending between a proximal end and a distal end;
an outer shaft having an outer shaft body forming an outer shaft bore, the outer shaft bore receiving the inner shaft, the outer shaft extending between a proximal end and a distal end, the outer shaft having a wire transition section proximate to the proximal end;
an exit path connector coupled to the outer shaft body at the wire transition section, the exit path connector having a rigid body section separate and discrete from the outer shaft body and coupled to the outer shaft body, the body section defining an exit path connector bore that receives the inner shaft, the body section having a side exit port at a side of the body section, the side exit port being open to the exit path connector bore, the body section including a front hub and a rear hub, the front hub having a larger diameter than the rear hub, a shoulder formed between the front hub and the rear hub, the side exit port passing through the shoulder; and
a catheter wire extending between the distal end and the proximal end of the outer shaft, the catheter wire passing through the side exit port from an interior of the exit path connector to an exterior of the cable exit port, the catheter wire extending within the outer shaft bore from the exit path connector to the distal end of the outer shaft.

24. The catheter assembly of claim 23, wherein the outer shaft is discontinuous at the wire transition section, the wire transition section including a forward section and a rearward section, the exit path connector being positioned between and connecting the forward section and the rearward section.

* * * * *